(12) United States Patent
Redinger

(10) Patent No.: US 7,322,953 B2
(45) Date of Patent: Jan. 29, 2008

(54) CATHETER DEVICE

(75) Inventor: Peter Redinger, Bainbridge Island, WA (US)

(73) Assignee: Covidien AG (CH)

( * ) Notice: Subject to any disclaimer, the term of this patent is extended or adjusted under 35 U.S.C. 154(b) by 582 days.

(21) Appl. No.: 10/634,111

(22) Filed: Aug. 4, 2003

(65) Prior Publication Data

US 2005/0033264 A1 Feb. 10, 2005

(51) Int. Cl.
*A61M 3/00* (2006.01)

(52) U.S. Cl. ........................................................ 604/43

(58) Field of Classification Search ............ 604/93.01, 604/264, 44, 43, 523, 27, 35, 41
See application file for complete search history.

(56) References Cited

U.S. PATENT DOCUMENTS

| 701,075 | A | | 5/1902 | McCully |
|---|---|---|---|---|
| 4,134,402 | A | | 1/1979 | Mahurkar ............... 128/214 R |
| 4,583,968 | A | | 4/1986 | Mahurkar .................... 604/43 |
| 4,675,004 | A | | 6/1987 | Hadford et al. .............. 604/44 |
| 4,682,978 | A | | 7/1987 | Martin ......................... 604/43 |
| 4,808,155 | A | | 2/1989 | Mahurkar .................... 604/43 |
| 4,842,582 | A | | 6/1989 | Mahurkar .................... 604/43 |
| 5,009,636 | A | | 4/1991 | Wortley et al. .............. 604/43 |
| 5,116,310 | A | * | 5/1992 | Seder et al. .................. 604/43 |
| 5,209,723 | A | | 5/1993 | Twardowski et al. ......... 604/43 |
| 5,221,256 | A | * | 6/1993 | Mahurkar .................... 604/43 |
| 5,374,245 | A | * | 12/1994 | Mahurkar .................... 604/43 |
| 5,403,291 | A | | 4/1995 | Abrahamson ............... 604/280 |
| 5,464,398 | A | | 11/1995 | Haindl ....................... 604/280 |
| 5,569,182 | A | | 10/1996 | Twardowski et al. ......... 604/43 |
| 5,571,093 | A | | 11/1996 | Cruz et al. .................. 604/270 |
| 5,685,867 | A | | 11/1997 | Twardowski et al. ....... 604/280 |
| 5,830,196 | A | | 11/1998 | Hicks ......................... 604/280 |
| 5,858,009 | A | | 1/1999 | Jonkman .................... 604/264 |
| 5,931,831 | A | | 8/1999 | Linder ........................ 604/523 |
| 5,961,486 | A | | 10/1999 | Twardowski et al. ......... 604/43 |
| 6,099,513 | A | * | 8/2000 | Spehalski ................... 604/264 |
| 6,409,700 | B1 | | 6/2002 | Siegel, Jr. et al. ............ 604/43 |
| 7,090,654 | B2 | * | 8/2006 | Lotito et al. ................. 604/43 |

FOREIGN PATENT DOCUMENTS

| EP | 0 623 356 | 11/1994 |
|---|---|---|
| FR | 2 326 941 | 5/1977 |
| WO | WO 92/14500 | 9/1992 |
| WO | WO 99/38550 | 8/1999 |

* cited by examiner

*Primary Examiner*—Nicholas D. Lucchesi
*Assistant Examiner*—Christopher Koharski
(74) *Attorney, Agent, or Firm*—Carter, Deluca, Farrell & Schmidt, LLP

(57) ABSTRACT

A catheter includes an elongated body having a first and second wall that defines at least one lumen. The first wall includes at least one outwardly extending ridge. The at least one ridge defines a lateral opening in the first wall and extends to the distal end of the body. The ridge is dimensioned and positioned to support a body vessel such that occlusion of the first lumen is substantially prevented.

14 Claims, 6 Drawing Sheets

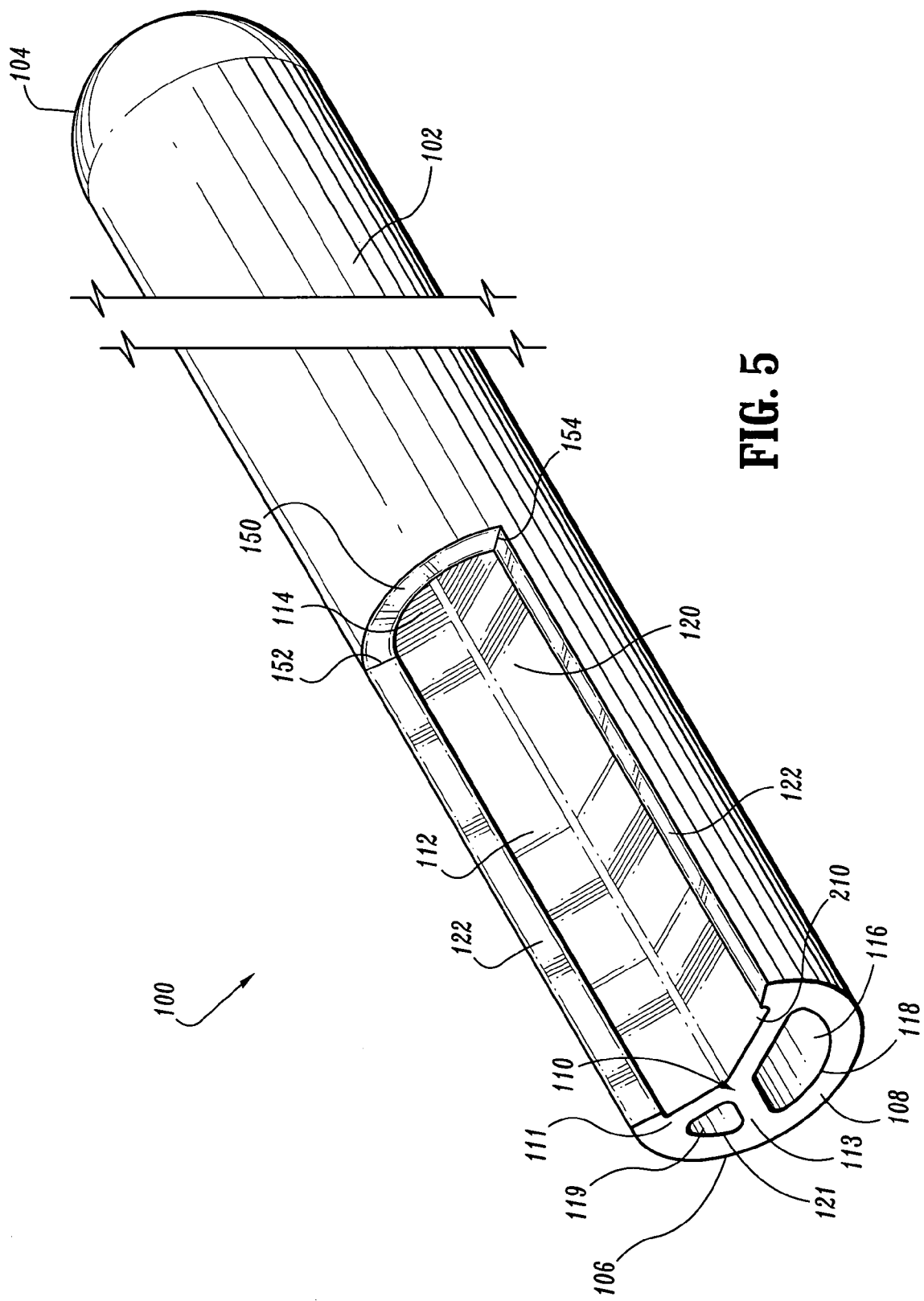

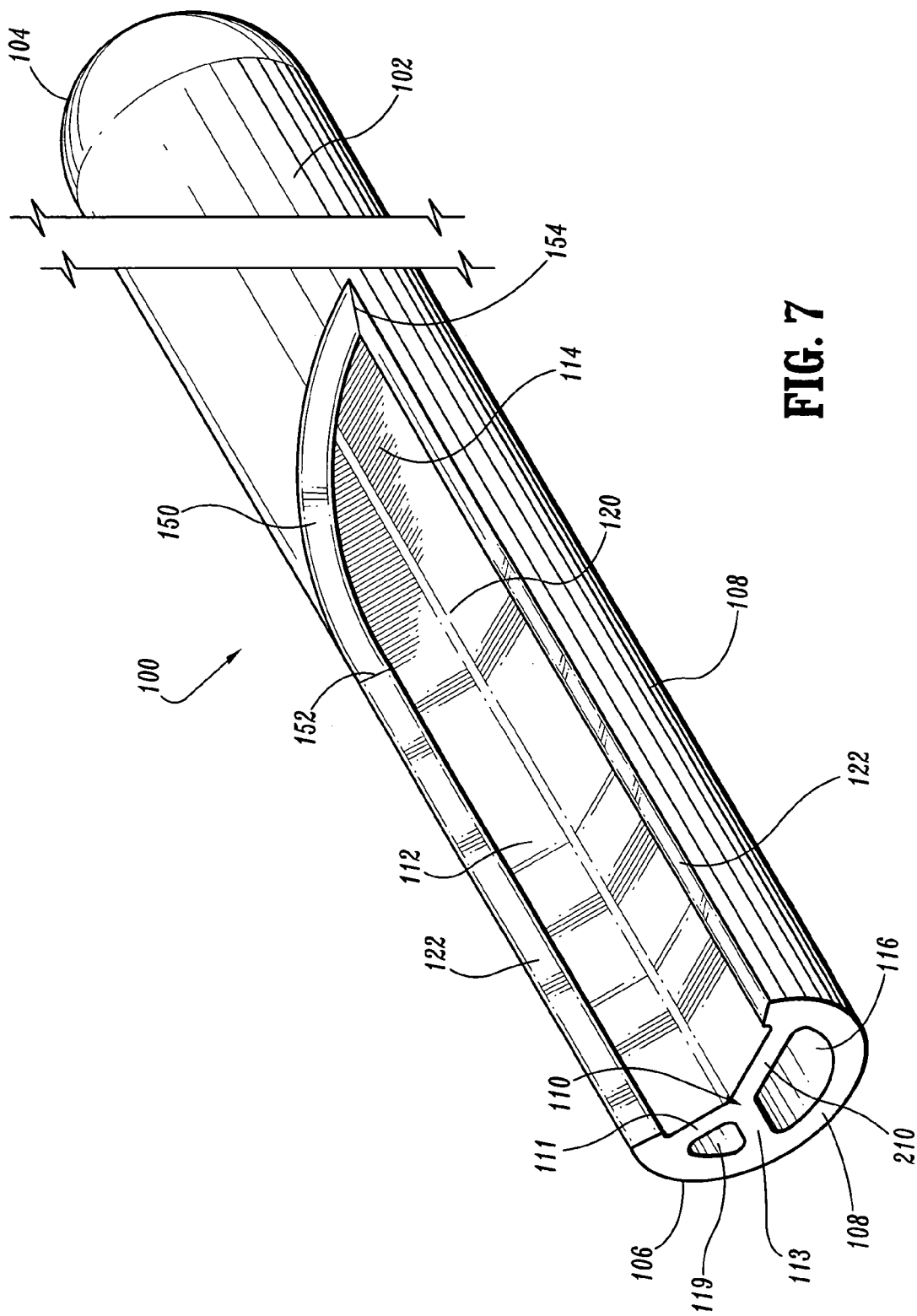

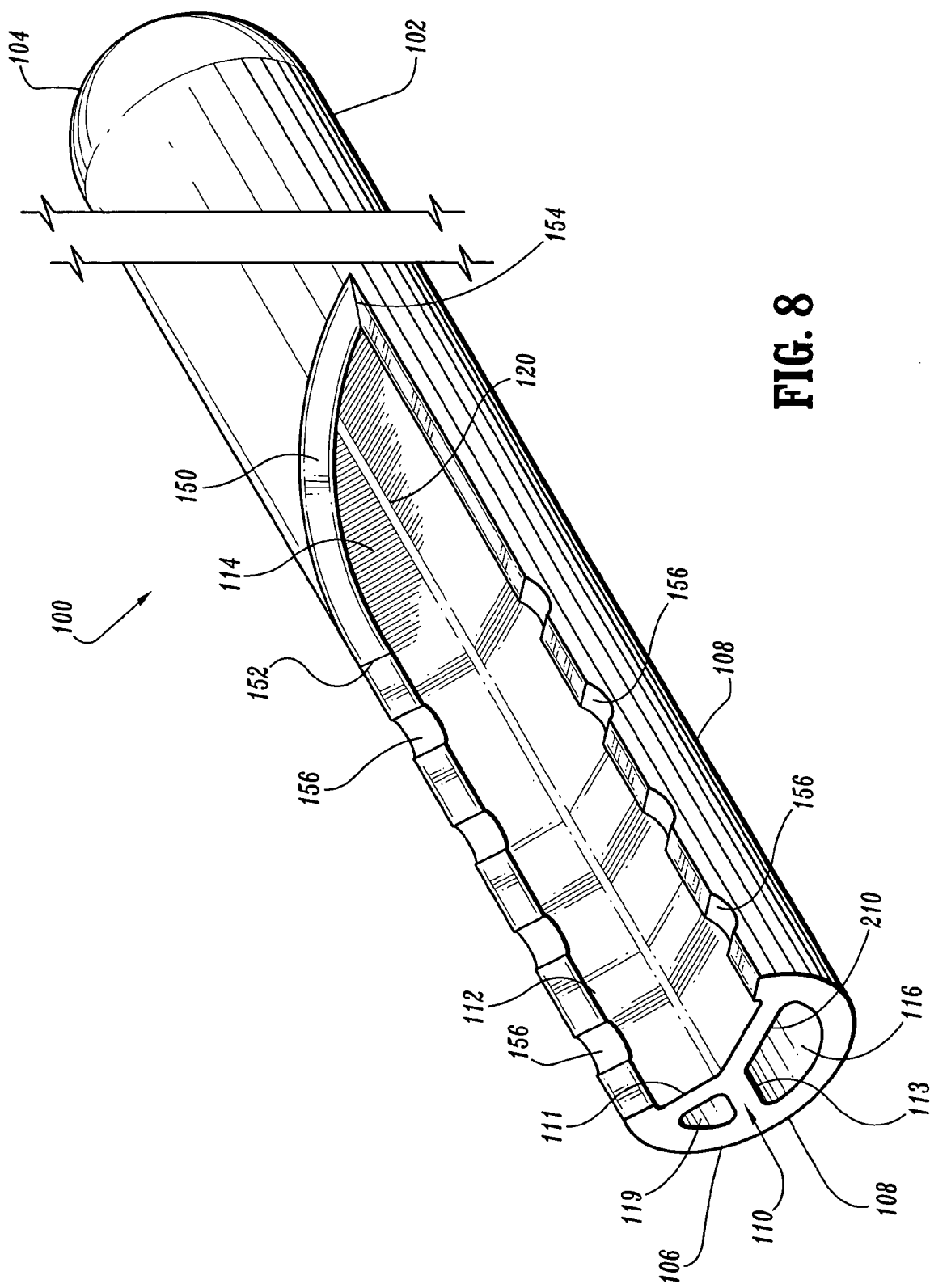

CATHETER DEVICE

BACKGROUND

1. Technical Field

The present disclosure relates generally to medical catheter apparatus, and more particularly to a catheter including support structure that prevents occlusion thereof during insertion within a body vessel, cavity, etc.

2. Description of the Related Art

Some known catheters are tubular, flexible medical devices for administration of fluids (withdrawal, introduction, etc.) with cavities, ducts, vessels, etc. of a body. Typically, catheter devices include a stylet, trocar, etc. that are inserted with the catheter device to facilitate puncturing the cavity of a body and provide support therefor. The stylet can be withdrawn to allow for administration of fluids with the body via the catheter device.

These catheter devices may be employed for administration of fluids that includes the simultaneous introduction and withdrawal of fluid for applications such as, surgery, treatment, diagnosis, etc. In one particular hemodialysis application, blood is withdrawn from a blood vessel for treatment by an artificial kidney device and the treated blood is introduced back into the blood vessel.

Various known catheter devices have been employed for simultaneous withdrawal and introduction of fluid with a body. These devices may utilize multiple lumens, such as dual lumen catheters that facilitate bidirectional fluid flow whereby one lumen performs withdrawal of blood and the other lumen introduces treated blood to the vessel. During an exemplary hemodialysis procedure, a multiple lumen catheter is inserted into with a body and blood is withdrawn through an arterial lumen of the catheter. This blood is supplied to a hemodialysis unit which performs dialysis, or cleans the blood to remove waste and excess water. The dialyzed blood is returned to the patient through a venous lumen of the catheter. Typically, the venous lumen is separated from the arterial lumen by an inner catheter wall, called a septum. The openings of the venous lumen and the arterial lumen are typically staggered to reduce recirculation of blood flow during the hemodialysis procedure.

The above mentioned catheter devices, however, can suffer from various drawbacks. For example, during a procedure, such as, for example, a prolonged use application, a wall of a blood vessel can cause the lumen ports, lumen walls, etc. of a catheter device to draw up portions of the blood vessel due to over flexibility, thin walls, etc. of the catheter device. This disadvantageously closes off the lumens, preventing fluid flow and results in complications, patient risk, etc. Another drawback may arise if the catheter is inserted improperly within the vessel or if post-insertion movement occurs. In these situations, suction introduced through the lumens may cause the lumen ports to draw portions of the vessel wall therein. This can disadvantageously result in flow occlusion.

Therefore, it would be desirable to overcome the disadvantages and drawbacks of the prior art with a catheter including support structure that prevents occlusion thereof during insertion within a body vessel, cavity, etc. to facilitate unobstructed fluid flow. It would be desirable if such a catheter included an outer wall having outwardly extending ridges that are configured and spaced apart to support a body vessel such that occlusion of the catheter is prevented. It would be highly desirable if the catheter and its constituent parts are easily and efficiently manufactured and assembled.

SUMMARY

Accordingly, a catheter is provided including support structure that prevents collapse thereof during insertion within a body vessel, cavity, etc. to facilitate unobstructed fluid flow to overcome the disadvantages and drawbacks of the prior art. Desirably, such a catheter includes an outer wall having outwardly extending ridges that are configured and spaced apart to support a body vessel such that occlusion of the catheter is prevented. Most desirably, the catheter is easily and efficiently manufactured and assembled. The present disclosure resolves related disadvantages and drawbacks experienced in the art.

The present disclosure provides, among other things, a vascular access device designed for insertion into a vessel of a body that allows for inflow and outflow of fluids, such as, for example, blood, medications, saline, etc. The vascular access device may have a tube, round, oval or other configuration and may contain more than one interior lumen for the flow of fluids. The vascular access device is designed with standoff ridges that prevent a vessel wall from deforming and occluding the inflow ports of the vascular access device when positioned inside the vessel. The ridges extend from the inlet (suction) port to the distal return port. The ridges may also be proximal to side holes formed in the vascular access device and protrude away from the surface of the cannula.

The non-distal inlet (suction) port and a lateral opening disposed adjacent thereto may include a helical configuration such that the distance from one end of the port to the distal end of the vascular access device is less than the distance from a second end of the port to the distal end of the vascular access device. The ridges can be scalloped out creating additional open area to prevent inlet occlusion.

In one particular embodiment, a catheter is provided, in accordance with the principles of the present disclosure. The catheter includes an elongated body extending from a proximal end to a distal end thereof. The body has a first wall and a second wall that define at least one lumen. The first wall includes at least one outwardly extending ridge. The at least one ridge defines a lateral opening in the first wall that extends to the distal end of the body. Desirably, the ridges are configured and spaced apart to support a body vessel such that occlusion of the at least one lumen is substantially prevented.

The first wall and the second wall may define a first lumen and a second lumen that extend along the body. The first lumen can include an inlet port disposed adjacent the lateral opening and the second lumen can include an outlet port disposed adjacent the distal end of the body. Alternatively, the first wall and the second wall define a first lumen, a second lumen and a third lumen such that the second wall includes a first portion that is disposed between the first lumen and the second lumen, a second portion that is disposed between the second lumen and the third lumen, and a third portion that is disposed between the third lumen and the first lumen.

The at least one ridge may include a pair of ridges extending from the first wall to define the lateral opening. The pair of ridges may define an angle with the second wall of less than 90°. The at least one lumen may include an outlet port that cooperates with the pair of ridges such that at least a portion of the lateral opening has a helical configuration. The at least one ridge may include a plurality of lateral channels.

The first wall may define a plurality of side openings. The lateral opening can be further defined by a port defined by the at least one lumen. The port has a first end and a second end. The port extends across the first wall such that the distance between the first end of the port and the distal end of the body is less than the distance between the second end of the port and the distal end of the body. Alternatively, the port extends across the first wall such that the distance between the first end of the port and the distal end of the body is substantially equal to the distance between the second end of the port and the distal end of the body.

In an alternate embodiment, the elongated body has an outer wall and an inner wall that define a first lumen having a first port, and a second lumen having a second port, that extend along the body. The outer wall includes a plurality of ridges outwardly extending from the outer wall and disposed adjacent to the first port of the first lumen. The plurality of ridges define a lateral opening in the outer wall that extends to the distal end of the body. The plurality of ridges are configured and spaced apart to support a body vessel such that occlusion of the first lumen and the second lumen is prevented. The plurality of ridges may be configured and spaced apart to support the body vessel such that occlusion of a third lumen is prevented.

BRIEF DESCRIPTION OF THE DRAWINGS

The objects and features of the present disclosure, which are believed to be novel, are set forth with particularity in the appended claims. The present disclosure, both as to its organization and manner of operation, together with further objectives and advantages, may be best understood by reference to the following description, taken in connection with the accompanying drawings, as set forth below.

FIG. 3 is a perspective view of the catheter shown in FIG. 1 having an alternate embodiment of an elongated body;

FIG. 4 is a perspective view of the catheter shown in FIG. 1 having an alternate embodiment of a lateral opening;

FIG. 5 is a perspective view of an alternate embodiment of the catheter shown in FIG. 1;

FIG. 7 is a perspective view of the catheter shown in FIG. 5 having an alternate embodiment of the lateral opening; and FIG. 8 is a perspective view of the catheter shown in FIG. 6 having an alternate embodiment of the ridges.

DETAILED DESCRIPTION OF THE EXEMPLARY EMBODIMENTS

The exemplary embodiments of the catheter and methods of use disclosed are discussed in terms of medical catheters for the administration of fluids (withdrawal, introduction, etc.) with the body of a subject and more particularly, in terms of a catheter including support structure that prevents occlusion thereof during insertion within a body vessel, cavity, etc. to facilitate unobstructed fluid flow. It is envisioned that the present disclosure may be employed with a range of catheter applications including surgical, diagnostic and related treatments of diseases, body ailments, etc. of a subject. It is further envisioned that the principles relating to the catheter disclosed include employment with various catheter related procedures, such as, for example, hemodialysis, cardiac, abdominal, urinary, intestinal, etc., in chronic, acute, etc. applications. It is contemplated that the catheter can be used for administration of fluids such as, for example, medication, saline, bodily fluids such as, blood, urine, etc.

In the discussion that follows, the term "proximal" will refer to the portion of a structure that is closer to a practitioner, while the term "distal" will refer to the portion that is further from the practitioner. As used herein, the term "subject" refers to a human patient or other animal. According to the present disclosure, the term "practitioner" refers to a doctor, nurse or other care provider and may include support personnel.

The following discussion includes a description of the catheter, in accordance with the principles of the present disclosure. Reference will now be made in detail to the exemplary embodiments of the disclosure, which are illustrated in the accompanying figures.

Figure 1:
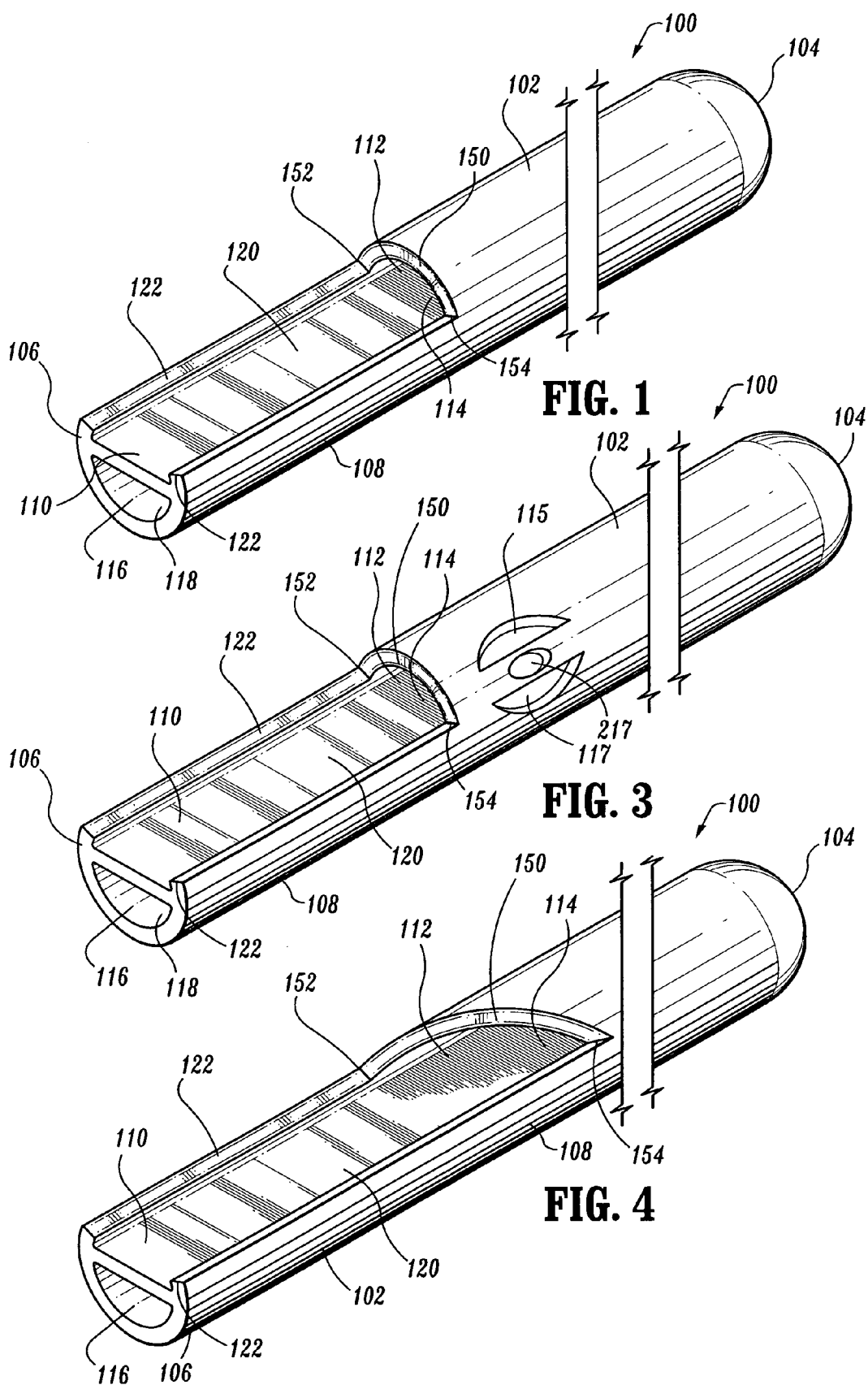
FIG. 1 is a perspective view of a catheter in accordance with the principles of the present disclosure.
Figure 2:
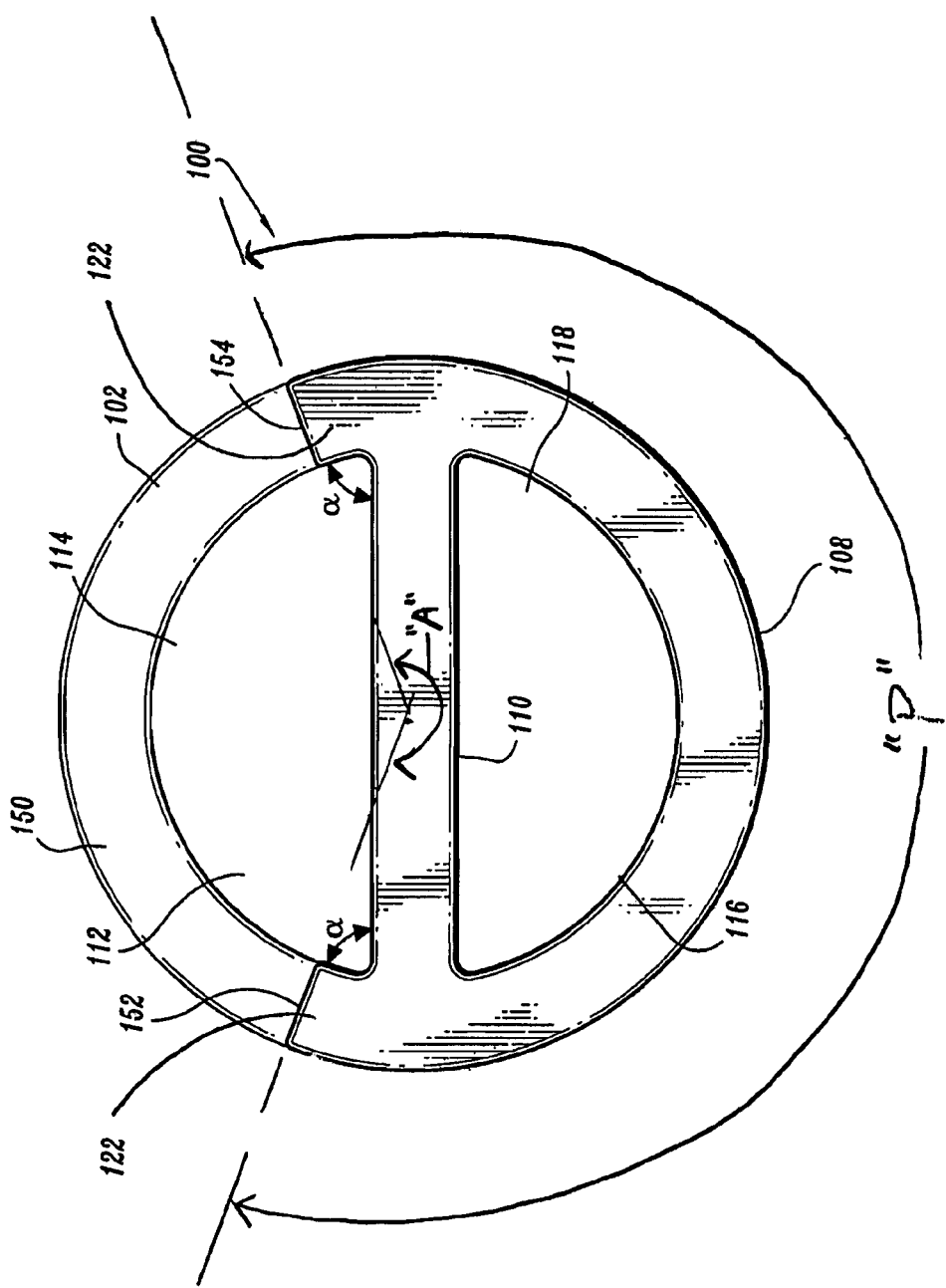
FIG. 2 is a front view, in part elevation, of a distal end of the catheter shown in FIG. 1.

Turning now to the figures, wherein like components are designated by like reference numerals throughout the several views. Referring initially to FIGS. 1 and 2, a catheter 100 includes an elongated body 102 extending from a proximal end 104 to a distal end 106. Elongated body 102 includes a first wall, such as, for example, an outer catheter wall 108 and a second wall, such as, for example, an inner wall, or septum 110. It is contemplated that the first wall may include an inner wall and the second wall may include an outer wall.

Outer catheter wall 108 includes a pair of standoff ridges 122 extending outwardly therefrom. Standoff ridges 122 define a lateral opening 120 in outer catheter wall 108 that extends to distal end 106. Standoff ridges 122 are advantageously configured and spaced apart to support a body vessel (not shown) such that occlusion of first lumen 112 and second lumen 116 is prevented to facilitate unobstructed fluid flow. One or a plurality of ridges may be employed. The wall portion of the outer catheter wall 108 adjacent the distal end 106 of the elongated body 102 defines a peripheral arc segment "p" which subtends an angle "A". Angle "A" may be at least 180°, or greater than 180°, to define the pair of standoff ridges 122 shown in FIG. 2.

Elongated body 102 has a cylindrical outer surface. It is contemplated that elongated body 102 may be variously dimensioned and attachable to other medical devices. It is further contemplated that the outer surface of elongated body 102 may have various configurations, such as, for example, rectangular, elliptical, polygonal, etc.

Lumens 112, 116 each may have a substantially D-shaped or semi-circular configuration. Lumens 112, 116 are elongated with body 102 and have inner surfaces configured to facilitate fluid flow within lumens 112, 116. It is contemplated that lumens 112, 116 may be configured for arterial and/or venous flow. It is envisioned that lumens 112, 116 may have various configurations, such as, for example, cylindrical, rectangular, elliptical, polygonal, etc. The first and second lumens may be configured for various forms of fluid flow in various directions and orientations, according to the requirements of a particular catheter application.

Lumens 112, 116 may be uniformly dimensioned or include alternative dimensional cross sections within elongated body 102, such as, narrow and broad portions, converging surfaces, undulating surfaces, etc. according to the particular flow indications and/or flow rate requirements. It is contemplated lumen 112 and lumen 116 may extend alternative lengths. It is further contemplated that elongated body 102 may include one or a plurality of lumens.

First lumen 112 includes a first port, such as, for example, an inlet port 114 that is recessed from distal end 106 of elongated body 102. Inlet port 114 may be disposed in a closer proximity to distal end 106. An outlet port (not shown) of first lumen 112 is disposed adjacent proximal end 104 of elongated body 102. Inlet port 114 is configured as a suction port and may be inserted with a blood vessel of a subject (not shown) such that blood is withdrawn, by for example, arterial blood flow in a first direction, from the blood vessel for treatment by an artificial kidney device (not shown). Inlet port 114 may be variously dimensioned and configured, such as, for example, rectangular, elliptical, polygonal, etc. and may include adapters, clips, etc. to facilitate fluid flow and/or attachment to other structure. It is contemplated that inlet port 114 is configured for expulsion of fluid.

First lumen 112 is separated from second lumen 116 by septum 110. Second lumen 116 includes a second port, such as, for example, an outlet port 118 disposed adjacent distal end 106. An inlet port (not shown) of second lumen 116 is disposed adjacent proximal end 104. Outlet port 118 is configured for expulsion of fluid and introduces the treated blood from the artificial kidney device back into the blood vessel, by for example, venous blood flow in a second opposite direction. Outlet port 118 may be variously dimensioned and configured, such as, for example, rectangular, elliptical, polygonal, etc. and may include adapters, clips, etc. to facilitate fluid flow and/or attachment to other structure. It is contemplated that outlet port 118 is configured for withdrawal of fluid.

The components of catheter apparatus 100 are fabricated from materials suitable for medical applications, such as, for example, polymerics or metals, such as stainless steel, depending on the particular catheter application and/or preference of a practitioner. Semi-rigid and rigid polymerics are contemplated for fabrication, as well as resilient materials, such as molded medical grade polypropylene. One skilled in the art, however, will realize that other materials and fabrication methods suitable for assembly and manufacture, in accordance with the present disclosure, also would be appropriate.

Standoff ridges 122 extend outwardly from outer catheter wall 108 for engagement with the wall of a body vessel that catheter 100 is inserted therewith. Standoff ridges 122 engage the wall of the body vessel for support thereof and are configured to prevent the body vessel from collapsing ports 114, 118 and other portions of lumens 112, 116. It is contemplated that standoff ridges 122 may extend variable lengths to engage a vessel wall. It is further contemplated that standoff ridges 122 may have sufficient thickness and/or be fabricated from semi-rigid or rigid materials to prevent undesired deformation of catheter 100.

Standoff ridges 122 extend from outer catheter wall 108 away from septum 110 so as to form a ridge angle α between septum 110 and standoff ridges 122. Although ridge angle α is shown as being less than 90°, ridge angle α may be any ridge angle α suitable to the desired purpose, such as, for example, 100°, 120°, etc. Ridge angle α disposes standoff ridges 122, relative to septum 110, to maintain the vessel wall in an orientation to prevent occlusion of inlet port 114 and first lumen 112. This configuration advantageously allows for continuous fluid flow.

Standoff ridges 122 define a lateral opening 120 in outer catheter wall 108. Lateral opening 120 extends to distal end 106 of elongated body 102. Inlet port 114 of first lumen 112 extends across outer catheter wall 108 and cooperates with standoff ridges 122 to define lateral opening 120. It is envisioned that lateral opening 120 may be variously sized and configured according to the particular catheter application. In an alternate embodiment, as shown in FIG. 3, outer catheter wall 108 defines a plurality of side openings, such as, for example, a first pressure port 115, a second pressure port 117 and a third pressure port 217. Ports 115, 117 and 217 communicate with second lumen 116 and prevent an excessive pressure buildup between first lumen 112 and second lumen 116. Ports 115, 117 and 217 also facilitate uniform fluid flow within catheter 100. It is contemplated that ports 115, 117 and 217 may be variously dimensioned and configured, such as, for example, rectangular, elliptical, polygonal, etc. and may include adapters, clips, etc. to facilitate fluid flow and/or attachment to other structure.

Lateral opening 120 defines a luminal cut 150 in outer catheter wall 108. Luminal cut 150 defines a first end, such as, for example, a cut start 152 and a second end, such as, for example, a cut stop 154 of lateral opening 120. Luminal cut 150 extends across catheter wall 108 such that the distance between cut start 152 and distal end 106 is approximately equal to the distance between cut stop 154 and distal end 106.

In an alternate embodiment, as shown in FIG. 4, lateral opening 120, similar to that described, includes a helically configured portion defined in cooperation with inlet port 114. Lateral opening 120 is defined by luminal cut 150 such that luminal cut 150 extends across catheter wall 108 in a helical configuration. Cut start 152 extends a distance from distal end 106 that is less than the distance between cut stop 154 and distal end 106. This configuration advantageously prevents occlusion of first lumen 114.

Figure 6:
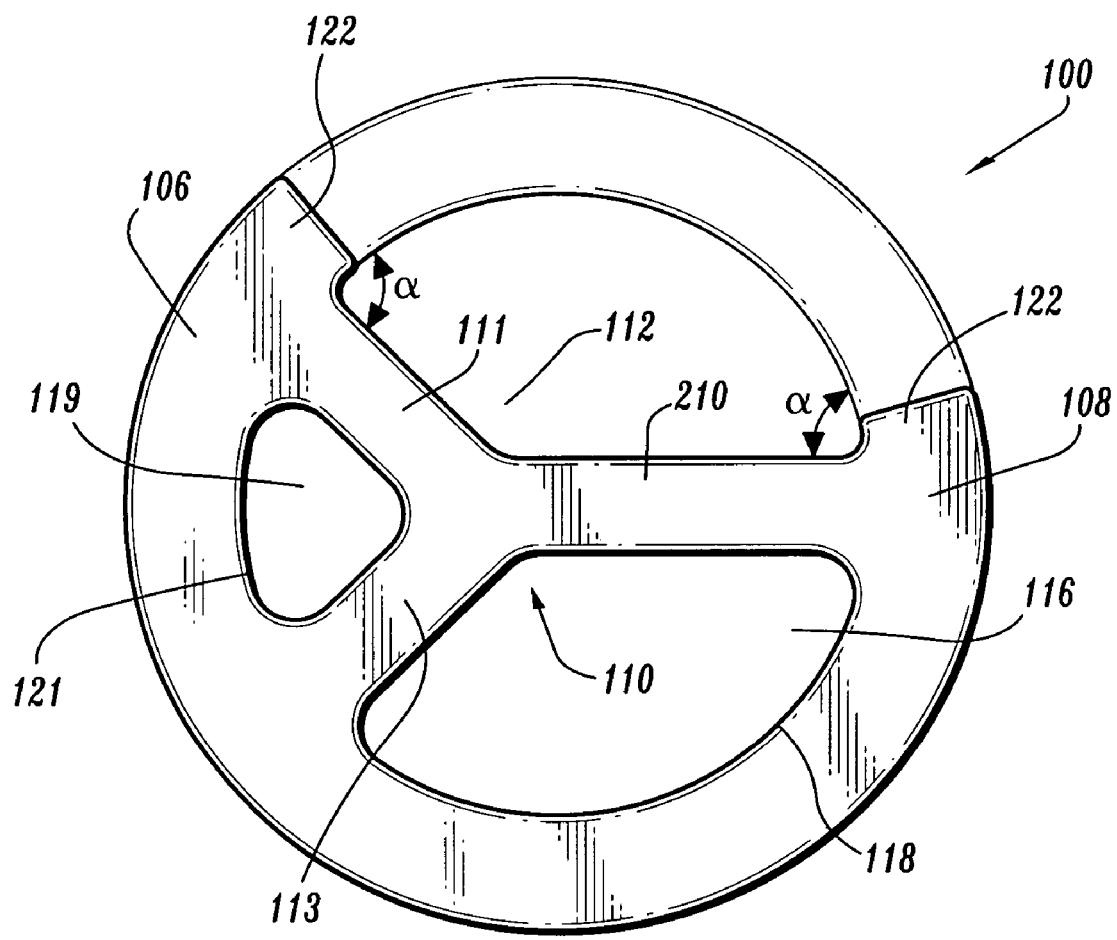
FIG. 6 is a front view of the distal end of the catheter shown in FIG. 5.

Referring to FIGS. 5 and 6, an alternate embodiment of catheter 100 is shown, similar to that described. Outer catheter wall 108 and septum 110 further define a third lumen 119. Third lumen 119 is configured to introduce fluids, such as, for example, medication, saline, etc. into a body vessel or may employed to monitor subject condition.

Third lumen 119 may have a substantially D-shaped or semi-circular configuration. Third lumen 119 is elongated with elongated body 102 and has inner surfaces configured to facilitate fluid flow. It is envisioned that third lumen 119 may have various configurations, such as, for example, cylindrical, rectangular, elliptical, etc. The third lumen may be configured for various forms of fluid flow in various directions and orientations, according to the requirements of a particular catheter application. Third lumen 119 may be uniformly dimensioned or include alternative dimensional cross sections within elongated body 102, such as, narrow and broad portions, converging surfaces, undulating surfaces, etc. according to the particular flow indications and/or flow rate requirements.

Septum 110 includes a first inner catheter wall 210, a second inner catheter wall 111 and a third inner catheter wall 113 that define lumens 112, 116 and 119, and facilitate fluid flow of catheter 100. First lumen 112 is separated from second lumen 116 by first inner catheter wall 210. Second lumen 116 is separated from third lumen 119 by second inner catheter wall 111. Third lumen 119 is separated from first lumen 112 by third inner catheter wall 113. First inner catheter wall 210, second inner catheter wall 111 and third inner catheter wall 113 may be relatively spaced apart to facilitate fluid flow according to the requirements of a particular catheter application.

Third lumen 119 includes a third port 121. Third port 121 is configured to introduce fluids into a body vessel from third lumen 119 or may employed to monitor subject condition. Third port 121 may be variously dimensioned and configured, such as, for example, rectangular, elliptical, polygonal, etc. and may include adapters, clips, etc. to facilitate fluid flow and/or attachment to other structure.

In an alternate embodiment of the triple lumen embodiment of catheter 100, as shown in FIG. 7, lateral opening 120 includes a helically configured portion, similar to that described, defined in cooperation with inlet port 114. Lateral opening 120 is defined by a luminal cut 150 such that luminal cut 150 extends across catheter wall 108 in a helical configuration. Cut start 152 extends a distance from distal end 106 that is less than the distance between cut stop 154 and distal end 106. This configuration advantageously prevents occlusion of first lumen 114. In another alternate embodiment of the triple lumen embodiment of catheter 100, as shown in FIG. 8, a plurality of lateral channels 156 are disposed along the length of standoff ridges 122, providing additional open area that prevents occlusion of inlet port 114.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A medical catheter, which comprises:
an elongated body adapted for insertion within a blood vessel, the elongated body including an outer wall defining a longitudinal axis and having leading and trailing end portions, and with at least one longitudinal lumen within the outer wall for passage of fluid, the leading end portion including an outer wall portion defining a peripheral arc segment and with a fluid port in fluid communication with the at least one longitudinal lumen, the peripheral arc segment defining opposed ridges, the ridges generally extending along the longitudinal axis, each ridge having an outer ridge surface dimensioned and positioned to engage interior wall portions of the blood vessel in supporting relation therewith to substantially minimize collapse of the vessel and occlusion of the fluid port, the outer ridge surface of at least one of the ridges defining a plurality of lateral channels therein, the lateral channels being longitudinally spaced relative to the longitudinal axis of the elongated body.

2. The medical catheter according to claim 1 wherein the peripheral arc segment is dimensioned to subtend an angle greater than about 180 degrees.

3. The medical catheter according to claim 1 wherein each of the outer ridge surfaces includes lateral channels.

4. The medical catheter according to claim 3 wherein the elongated body includes first and second longitudinal lumens and respective fluid ports in fluid communication with the first and second longitudinal lumens to permit passage of fluid.

5. The medical catheter according to claim 4 wherein the fluid ports of the first and second longitudinal lumens are arranged in longitudinal spaced relation with respect to the longitudinal axis.

6. The medical catheter according to claim 4 wherein the elongated body includes an inner septum wall.

7. The medical catheter according to claim 6 wherein the outer ridges surfaces are each substantially planar, the lateral channels forming concavities within the outer ridge surfaces.

8. The medical catheter according to claim 7 wherein the outer ridges surfaces are each arranged in oblique relation with respect to the inner septum wall.

9. The medical catheter according to claim 1 wherein the elongated body includes three longitudinal lumens.

10. The medical catheter according to claim 1 wherein the elongated body includes a port wall adjacent the fluid port, the port wall defining a general helical arrangement with respect to the longitudinal axis.

11. The medical catheter according to claim 1 wherein the trailing end portion of the outer wall of the elongated body is substantially circular.

12. The medical catheter according to claim 1 wherein the trailing end portion of the outer wall of the elongated body is substantially elliptical.

13. A medical catheter, which comprises:
an elongated body adapted for insertion within a blood vessel of a subject, the elongated body including an outer wall defining a longitudinal axis and having proximal and distal ends, the elongated body having a first longitudinal lumen and associated fluid port for removal of blood from the subject and a second longitudinal lumen and associated fluid port for return of blood to the subject, the outer wall having an outer wall portion adjacent the distal end of the elongated body, the outer wall portion defining a peripheral arc segment subtending an angle greater than about 180 degrees to define opposed standoff ridges generally extending along the longitudinal axis, each ridge having an outer ridge surface dimensioned and positioned to engage interior wall portions of the blood vessel in supporting relation therewith to substantially minimize collapse of the vessel and occlusion of the fluid port, the outer ridge surfaces each defining a plurality of lateral channels therein, the lateral channels being longitudinally spaced relative to the longitudinal axis of the elongated body.

14. The medical catheter according to claim 13 wherein the fluid port associated with the second longitudinal lumen is distal of the fluid port associated with the first longitudinal lumen.

* * * * *